(12) United States Patent
Wallenstein et al.

(10) Patent No.: US 8,449,585 B2
(45) Date of Patent: May 28, 2013

(54) SEMI-CONSTRAINED BONE SCREW

(75) Inventors: Todd Wallenstein, Ashburn, VA (US);
Larry McClintock, Gore, VA (US);
Scott Jones, McMurray, PA (US);
Megan E. McMullen, Leesburg, VA
(US); Adam Wassinger, Reston, VA
(US)

(73) Assignee: K2M, Inc., Leesburg, VA (US)

( * ) Notice: Subject to any disclaimer, the term of this patent is extended or adjusted under 35 U.S.C. 154(b) by 203 days.

(21) Appl. No.: 12/940,531

(22) Filed: Nov. 5, 2010

(65) Prior Publication Data

US 2011/0106172 A1 May 5, 2011

Related U.S. Application Data

(60) Provisional application No. 61/258,379, filed on Nov. 5, 2009.

(51) Int. Cl.
*A61B 17/84* (2006.01)

(52) U.S. Cl.
USPC .............. 606/328; 606/300; 606/309

(58) Field of Classification Search
USPC .............. 606/60, 282, 286, 287, 288, 289, 606/290, 291, 300, 301, 328; 411/383, 396, 411/413
See application file for complete search history.

(56) References Cited

U.S. PATENT DOCUMENTS

| | | | |
|---|---|---|---|
| 3,054,321 A | 9/1962 | Macchia | |
| 4,237,363 A * | 12/1980 | Lemelson | 219/121.85 |
| 5,042,982 A | 8/1991 | Harms et al. | |
| 5,053,036 A | 10/1991 | Perren et al. | |
| 5,057,111 A | 10/1991 | Park | |
| 5,085,660 A | 2/1992 | Lin | |
| 5,269,784 A | 12/1993 | Mast | |
| 5,443,467 A | 8/1995 | Biedermann et al. | |
| 5,520,690 A | 5/1996 | Errico et al. | |
| 5,531,746 A | 7/1996 | Errico et al. | |
| 5,536,127 A | 7/1996 | Pennig | |
| 5,591,166 A | 1/1997 | Bernhardt et al. | |
| 5,607,426 A | 3/1997 | Ralph et al. | |
| 5,607,428 A | 3/1997 | Lin | |
| 5,643,265 A | 7/1997 | Errico et al. | |
| 5,827,285 A * | 10/1998 | Bramlet | 606/60 |
| 5,876,402 A | 3/1999 | Errico et al. | |
| 5,888,204 A | 3/1999 | Ralph et al. | |
| 5,904,683 A | 5/1999 | Pohndorf et al. | |
| 5,954,722 A | 9/1999 | Bono | |
| 5,976,141 A | 11/1999 | Haag et al. | |
| 6,016,727 A | 1/2000 | Morgan | |
| 6,022,350 A | 2/2000 | Ganem | |
| 6,099,531 A | 8/2000 | Bonutti | |
| 6,129,730 A | 10/2000 | Bono et al. | |
| 6,152,927 A | 11/2000 | Farris et al. | |

(Continued)

*Primary Examiner* — Kevin T Truong
*Assistant Examiner* — Christian Sevilla
(74) *Attorney, Agent, or Firm* — Carter, DeLuca, Farrell & Schmidt, LLP

(57) ABSTRACT

A bone screw for attaching a bone plate to bone includes a shank defining a lumen extending at least partially therethrough from a proximal end thereof, a head defining a lumen therethrough, and a rod member. The rod member is configured for insertion through the lumen of the head and into the lumen of the shank. The rod member is fixedly engageable with the shank and moveably coupled to the head such that both the rod member and the shank are moveable with respect to the head.

19 Claims, 6 Drawing Sheets

U.S. PATENT DOCUMENTS

| | | |
|---|---|---|
| 6,187,005 B1 | 2/2001 | Brace et al. |
| 6,206,882 B1 | 3/2001 | Cohen |
| 6,235,033 B1 | 5/2001 | Brace et al. |
| 6,290,703 B1 | 9/2001 | Ganem |
| 6,306,136 B1 | 10/2001 | Baccelli |
| 6,306,140 B1 | 10/2001 | Siddiqui |
| 6,322,562 B1 | 11/2001 | Wolter |
| 6,342,074 B1 | 1/2002 | Simpson |
| 6,364,880 B1 | 4/2002 | Michelson |
| 6,423,063 B1 | 7/2002 | Bonutti |
| 6,454,769 B2 | 9/2002 | Wagner et al. |
| 6,558,423 B1 | 5/2003 | Michelson |
| 6,565,567 B1 | 5/2003 | Haider |
| 6,595,993 B2 | 7/2003 | Donno et al. |
| 6,602,254 B2 | 8/2003 | Gertzbein et al. |
| 6,629,998 B1 | 10/2003 | Lin |
| 6,663,635 B2 | 12/2003 | Frigg et al. |
| 6,679,883 B2 | 1/2004 | Hawkes et al. |
| 6,716,214 B1 | 4/2004 | Jackson |
| 6,767,351 B2 | 7/2004 | Orbay et al. |
| 6,780,186 B2 | 8/2004 | Errico et al. |
| 6,893,444 B2 | 5/2005 | Orbay |
| 6,936,051 B2 | 8/2005 | Michelson |
| 6,955,677 B2 | 10/2005 | Dahners |
| 6,969,390 B2 | 11/2005 | Michelson |
| 6,972,019 B2 | 12/2005 | Michelson |
| 6,979,334 B2 | 12/2005 | Dalton |
| 6,984,234 B2 | 1/2006 | Bray |
| 7,001,385 B2 | 2/2006 | Bonutti |
| 7,001,389 B1 | 2/2006 | Navarro et al. |
| 7,033,394 B2 | 4/2006 | Michelson |
| 7,041,135 B2 | 5/2006 | Michelson |
| 7,048,739 B2 | 5/2006 | Konieczynski et al. |
| 7,077,864 B2 | 7/2006 | Byrd, III et al. |
| 7,163,538 B2 | 1/2007 | Altarac et al. |
| 7,175,624 B2 | 2/2007 | Konieczynski et al. |
| 7,229,443 B2 | 6/2007 | Eberlein et al. |
| 7,311,712 B2 | 12/2007 | Dalton |
| 7,318,825 B2 | 1/2008 | Butler et al. |
| 7,527,640 B2 | 5/2009 | Ziolo et al. |
| 7,651,517 B2 | 1/2010 | Konieczynski et al. |
| 2001/0021851 A1 | 9/2001 | Eberlein et al. |
| 2002/0042615 A1* | 4/2002 | Graf et al. .............. 606/73 |
| 2002/0045896 A1 | 4/2002 | Michelson |
| 2002/0128654 A1 | 9/2002 | Steger et al. |
| 2003/0130737 A1 | 7/2003 | McGahan et al. |
| 2004/0138662 A1 | 7/2004 | Landry et al. |
| 2006/0041260 A1 | 2/2006 | Orbay |
| 2006/0100625 A1 | 5/2006 | Ralph et al. |
| 2006/0149251 A1 | 7/2006 | Ziolo et al. |
| 2006/0200147 A1 | 9/2006 | Ensign et al. |
| 2007/0073298 A1 | 3/2007 | Beutter et al. |
| 2007/0213729 A1* | 9/2007 | Lindemann et al. ........ 606/69 |
| 2007/0233122 A1* | 10/2007 | Denis et al. ............ 606/73 |
| 2008/0215097 A1 | 9/2008 | Ensign et al. |
| 2008/0234677 A1 | 9/2008 | Dahners et al. |
| 2008/0249624 A1 | 10/2008 | Josimovic-Alasevic et al. |
| 2010/0137919 A1 | 6/2010 | Wolter |

\* cited by examiner

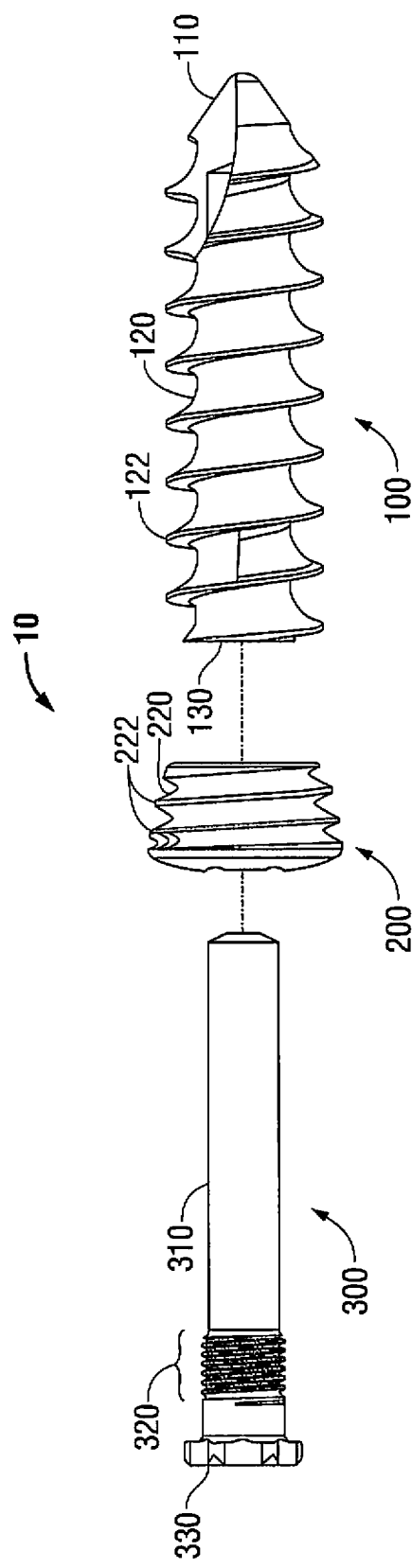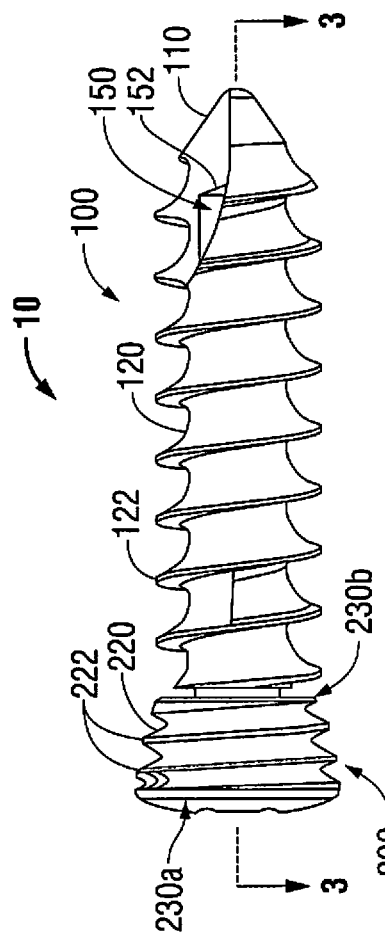

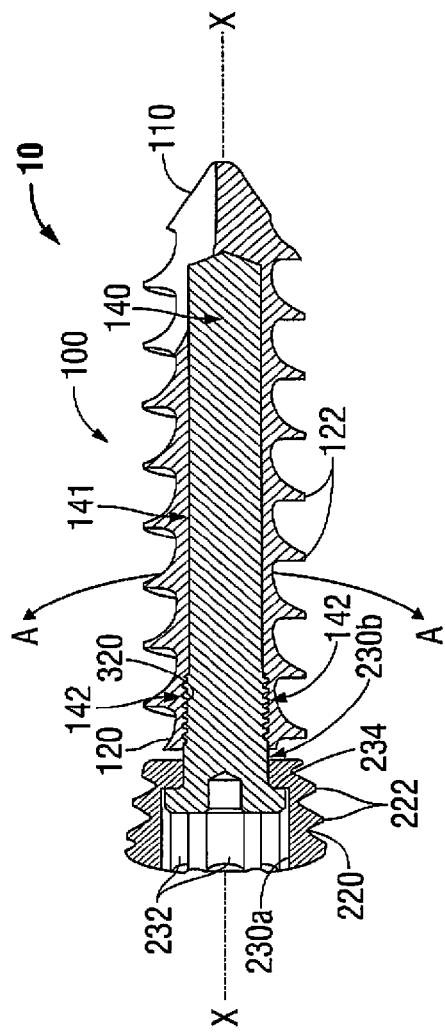
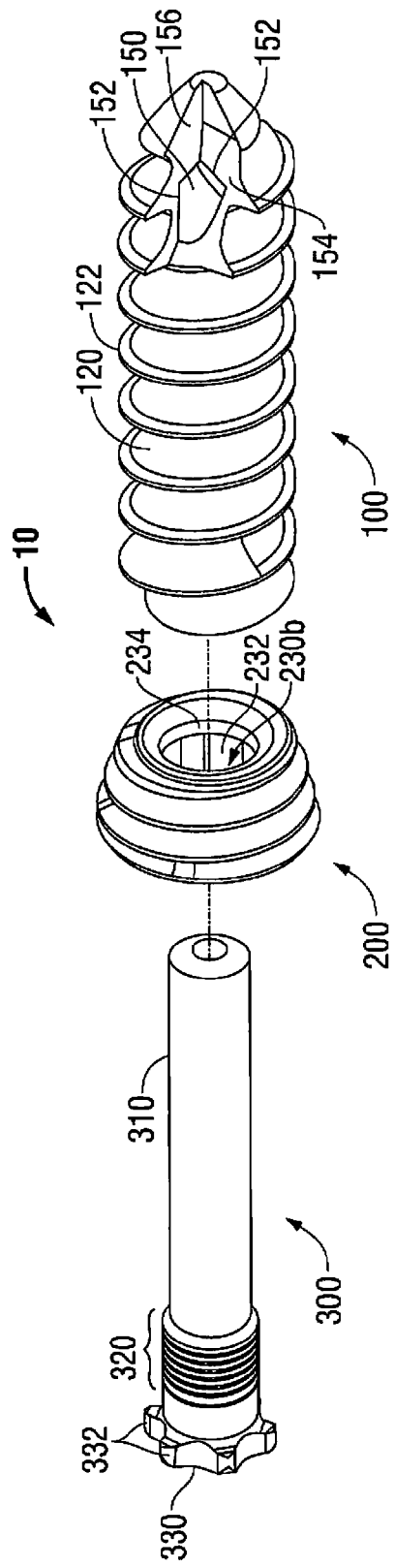

SEMI-CONSTRAINED BONE SCREW

CROSS-REFERENCE TO RELATED APPLICATIONS

This application claims the benefit of, and priority to, U.S. Provisional Patent Application Ser. No. 61/258,379 filed on Nov. 5, 2009, the entire contents of which are hereby incorporated by reference herein.

BACKGROUND

1. Technical Field

The present disclosure relates to a bone screw and, more particularly, to a semi-constrained bone screw for use with an implant, such as a bone plate.

2. Background of Related Art

The human spinal column is a highly complex structure. It includes more than twenty discrete bones, known as vertebrae, coupled sequentially to one another to house and protect critical elements of the nervous system. The cervical portion of the spine, which comprises the top of the spine up to the base of the skull, includes the first seven vertebrae.

For many reasons, such as aging and trauma, the intervertebral discs may begin to deteriorate and weaken, potentially resulting in chronic pain, degenerative disc disease, or even tearing of the disc. Ultimately, the disc may deteriorate or weaken to the point of tearing and herniation, in which the inner portions of the disc protrude through the tear. A herniated disc may press against, or pinch, the spinal nerves, thereby causing radiating pain, numbness, tingling, and/or diminished strength or range of motion.

Many treatments are available to remedy these conditions, including surgical procedures in which one or more damaged intervertebral discs are removed and replaced with a prosthetic. However, should the prosthetic protrude from the adjacent vertebrae and thereby contact the surrounding nerves or tissues, the patient may experience additional discomfort. In procedures for remedying this problem, a spinal plate assembly having one or more apertures and one or more bone screws is affixed to the vertebrae and oriented to inhibit such protrusion.

A common problem associated with the use of such a spinal plate assembly is the tendency of the bone screws to "back out" or pull away or otherwise withdraw from the bone into which they are mounted. This problem occurs, primarily, due to the normal torsional and bending motions of the body and spine. As the screws become loose and pull away or withdraw from the bone, the heads of the screws can rise above the surface of the plate assembly, which results in pain and discomfort for the patient or possibly the separation of the spinal plate from one or more vertebrae.

SUMMARY

In accordance with the present disclosure, a bone screw for attaching a bone plate to bone is provided. The bone screw includes a shank, a head, and a rod member. The shank has a lumen extending partially therethrough from a proximal end of the shank. The head also has a lumen extending therethrough. The rod member is configured to be inserted through the lumen of the head and into the lumen of the shank. The rod member is fixedly engageable with the shank and moveably coupled to the head such that both the rod member and the shank are moveable with respect to the head.

In one embodiment, a helical thread is formed on an outer surface of the shank to facilitate insertion of the bone screw into bone.

In another embodiment, the rod member includes a neck portion at a distal end of the rod member. The neck portion is threadably engageable with an inner surface of the shank.

In yet another embodiment, the rod member includes an outwardly protruding annular flange disposed at a proximal end of the neck portion. The annular flange is complementary in shape to an inner surface of the head and is configured to sit on a shoulder positioned on the inner surface of the head.

In still yet another embodiment, the head is configured to fixedly engage a bone plate. When the head is engaged with the bone plate, the rod member and the shank are moveable with respect to the head and the bone plate.

In still another embodiment, a helical thread is formed on an outer surface of the head for coupling with an opening in the bone plate.

In yet another embodiment, the head is constructed of a material which is harder than a material of a lip formed in or near the opening in the bone plate.

In accordance with another embodiment of the present disclosure, a bone plate assembly is provided. The bone plate assembly includes a bone plate and one or more bone screws. The bone plate includes a plurality of openings therein configured for insertion of a bone screw therethrough. Each bone screw includes a shank, a head, and a rod member. The shank has an open proximal end and includes a lumen extending partially therethrough. A continuous helical thread is disposed on an outer surface of the shank. The head has a lumen extending therethrough and includes a plurality of slots defined within an inner surface of the head. The head is securable within one of the openings in the bone plate. The rod member includes a distal shaft and a proximal portion. The proximal portion includes a plurality of outwardly protruding flanges shaped complementarily to the plurality of slots within the inner surface of the head. The distal shaft is insertable through the lumen of the head and into the lumen of the shank. The distal shaft of the rod member is fixedly engageable with the shank, while the plurality of flanges are configured to sit within the plurality of complementary-shaped slots such that the rod member and the shank are moveable with respect to the head.

In another embodiment, the bone plate includes a plurality of sections that are moveable with respect one another such that the bone plate is moveable between an expanded and a contracted position. Alternatively, the bone plate may be a unitary structure with fixed dimensions.

BRIEF DESCRIPTION OF THE DRAWINGS

Embodiments of the presently disclosed spinal plate and screw assembly are described herein with reference to the accompanying drawings, wherein:

FIG. 1 is a side view of a bone screw according to an embodiment of the present disclosure with parts separated;

FIG. 2 is a side view of the bone screw of FIG. 1 as assembled for use;

FIG. 3 is a side, cross-sectional view of the bone screw of FIG. 1 taken along section line 3-3 of FIG. 2;

FIG. 4 is an exploded perspective view of the bone screw of FIG. 1;

DETAILED DESCRIPTION

Figure 5:
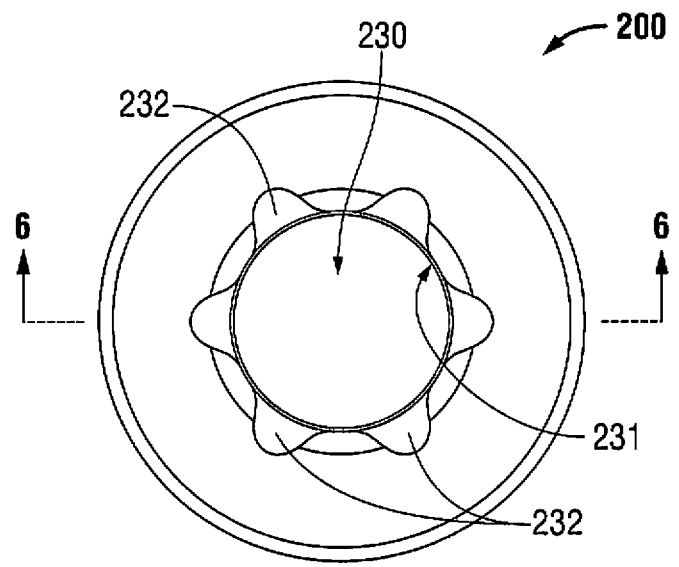
FIG. 5 is a top view of the head of the bone screw of FIG. 1.

Various embodiments of the presently disclosed semi-constrained screw and bone implant (e.g. cervical plate assembly) will now be described in detail with reference to the drawings, wherein like reference numerals identify similar or identical elements. In the drawings and in the description that follows, the term "proximal," will refer to the end of a device or system that is closest to the operator, while the term "distal" will refer to the end of the device or system that is farthest from the operator.

Figure 6:
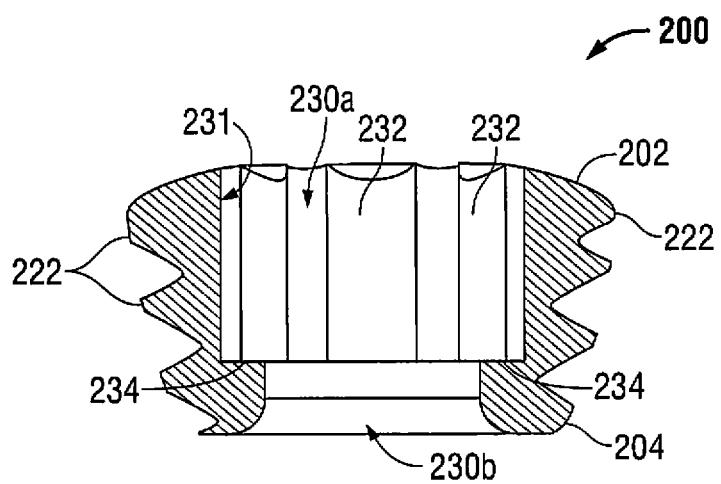
FIG. 6 is a side, cross-sectional view of the head of the bone screw of FIG. 1 taken along section line 6-6 of FIG. 5.
Figure 7A:
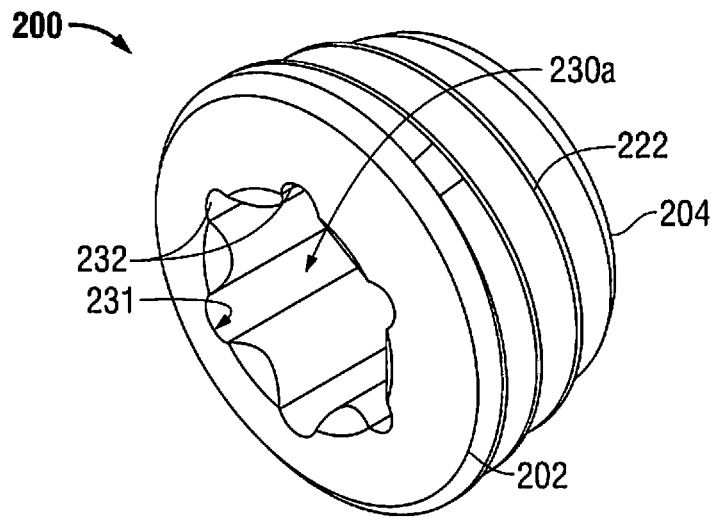
FIG. 7A is a top perspective view of the head of the bone screw of FIG. 1.

Referring initially to FIGS. 1 and 4, bone screw 10 generally includes shank 100, head 200, and rod member 300. Shank 100 includes a distal tip portion 110, an elongated body portion 120, and an open proximal end 130. Distal tip portion 110 is generally conically-shaped to facilitate insertion of bone screw 10 into bone. Elongated body portion 120 of shank 100 has a substantially uniform outer diameter and includes a continuous helical thread 122 formed thereon to allow for threaded insertion and retention of bone screw 10 within bone. A lumen 140 (FIG. 3) extends distally from the open proximal end 130 of the shank 100 partially therethrough. Head 200 of bone screw 10 is generally frustoconical in shape and includes two chambers 230a and 230b (FIG. 6), the first chamber 230a having a diameter greater than the diameter of the second chamber 230b such that a shoulder 234 is defined between the first and second chambers 230a and 230b, respectively (FIG. 6). A helical threading 222 is disposed on an outer surface 220 of head 200. Further, a plurality of longitudinal slots 232 are defined on an inner surface 231 of first chamber 230a of head 200, as best seen in FIG. 7A. Rod member 300 of bone screw 10 includes a distal shaft 310, a threaded neck 320, and a proximal flange portion 330 extending radially outward from rod member 300. It is contemplated that the head 200 may be formed from a different material than the material of the shank 100 such that the bone screw 10 is formed from mixed metals/alloys. Examples of suitable materials include titanium, titanium alloys (e.g., Ti-6Al-4V), stainless steel, and cobalt chrome alloys. By way of example only, the head may be formed of titanium alloy and the shank may be formed of commercially pure titanium.

Figure 7B:
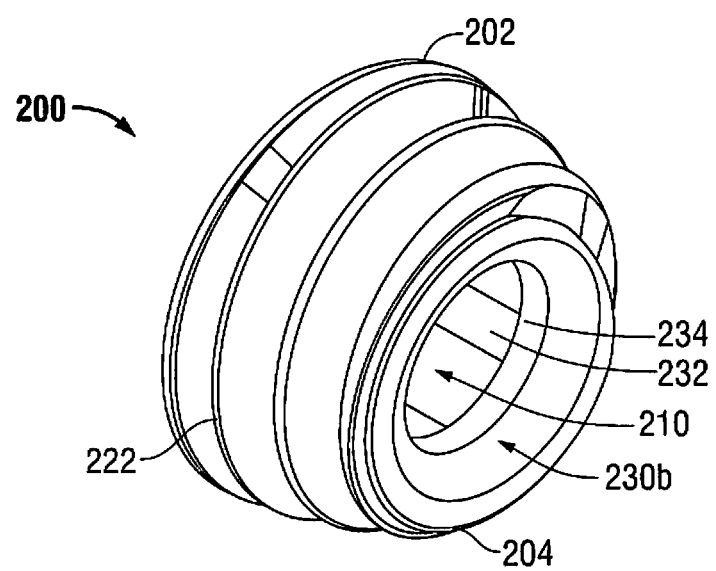
FIG. 7B is a bottom perspective view of the head of the bone screw of FIG. 1.

Referring now to FIGS. 2 and 3, helical thread 122 formed on elongated body portion 120 of shank 100 is preferably continuous and has a substantially uniform pitch. Similarly, helical thread 222 on outer surface of head 200 is preferably continuous and has a substantially uniform pitch, with the pitch of thread 122 preferably being greater than the pitch of thread 222. As best seen in FIGS. 3 and 7B, shank 100 and head 200 each include a respective lumen 140, 210. Lumen 140 and the proximal opening of second chamber 230b may have a substantially equal diameter and are defined centrally within shank 100 and head 200, respectively. Inner surface of shank 100 includes a threaded portion 142 disposed toward a proximal end of lumen 140, while, as discussed above, inner surface 231 of first chamber 230a of head 200 includes a plurality of longitudinal slots 232 defined therein. As mentioned above, a shoulder 234 is defined between first chamber 230a and second chamber 230b.

With reference now to FIGS. 1-4, distal shaft 310 of rod member 300 is insertable through first and second chambers 230a and 230b, respectively, of head 200 and into lumen 140 of shank 100. As shaft 310 is inserted further through head 200 and into lumen 140, threaded neck 320 of shaft 310 is eventually positioned adjacent threaded portion 142 of inner surface 141 of shank 100. From this position, rod member 300 and shank 100 may be rotated relative to one another to engage threads 142 with threads 320 thereby fixedly engaging shank 100 with rod member 300. At the same time, proximal flange portion 330 of rod member 300 enters first chamber 230a of head 200. As shown in the drawings, proximal flange portion 330 includes six protrusions 332 defining a generally hexagonal configuration. Slots 232 defined on inner surface 231 of first chamber 230a of head 200 define a complementary hexagonal shape. Although proximal flange portion 330 is illustrated with six protrusions 332, it is contemplated that a greater or lesser number of protrusions 332 may be formed in the proximal flange portion 330 with a corresponding number of slots 232 being formed on inner surface 231 of the head 200 such that the proximal flange portion 330 and the first chamber 230a have complementary configurations. As can be appreciated, the mating of protrusions 332 and slots 232 permits axial translation of rod member 300 with respect to head 200 along axis X-X, while inhibiting rotation of rod member 300 with respect to head 200 about axis X-X. Shoulder 234, defined between first chamber 230a and second chamber 230b, acts as a stop, inhibiting rod member 300 from translating further distally through head 200. Accordingly, once rod member 300 is engaged with shank 100 via the engagement of threads 142 and 320, head 200 is retained therebetween. Although head 200 is retained between shank 100 and rod member 300, head portion 200 is axially translatable between a first position wherein shoulder 234 and proximal flange portion 330 abut one another to inhibit further axial translation in the proximal direction and a second position wherein a distal portion of head 200 contacts the proximal end 120 of shank 100, preventing further axial translation in the distal direction. Furthermore, due to the configuration of proximal flange portion 330 of rod member 300 and first chamber 230a of head 200, rod member 300 and shank 100 are also moveable a sufficient distance in the radial direction with respect to head 200 to accommodate angulation of the shank relative to the head, as described more fully below.

Referring to FIG. 3, shank 100 of bone screw 10 is angularly pivotable relative to head 200 and longitudinal axis X-X as indicated by directional arrows A. Since the diameter of the first chamber 230a is greater than an outside diameter of the protrusions 332 of the proximal flange 330 of the rod member 300 and the diameter of second chamber 230b increases from its proximal opening to its distal opening, as describe more fully hereinbelow, rod member 300 is pivotable relative to the head 200. A first space is defined between the outer diameter of the protrusions 332 and the corresponding slots 232, and a second space is defined between the outer diameter of the proximal flange 330 and inner surface 231 of first chamber 230a. Additionally, a third space is defined between an outer surface of elongated body portion 310 (FIG. 4) and an inner surface of second chamber 230b. The first, second, and third spaces permit a range of angular movement between rod member 300 and head 200 as shown by directional arrows A. Thus, when assembled as bone screw 10, shank 100 is also angularly pivotable relative to head 200 as indicated by directional arrows A. In one embodiment, shank 100 is pivotable relative to head 200 and axis X-X in a cone with a total range of angulation of about 10°. Other ranges of angulation are also contemplated.

Although the complementary shaped protrusions 332 and slots 232 of rod member 300 and head 200, respectively, are described and shown as defining a hexagonal configuration, it is envisioned that alternate configurations may be provided so long as rod member 300 and shank 100 are axially translatable and radially moveable, but not rotatable, with respect to head 200.

Once rod member 300 is threadably engaged with shank 100, with head 200 disposed therebetween, as described above, distal end of rod member 300 is preferably laser welded to shank 100 along flute cuts 152 of flutes 150. One or more windows may be formed through the outer surface of the shank to facilitate laser welding or joining of the rod member 300 and the shank 100. FIG. 4 illustrates a window extending through a flute, but it is also contemplated that such a welding access window may be formed at any convenient location along the shank to facilitate welding the rod to the shank. Alternatively, other techniques for securing the rod member 300 and the shank 100 are contemplated. These alternate techniques include swaging, friction fit (i.e. tapered lumen 140), etc. The laser welding of shank 100 to rod member 300 fixes screw 10 in its assembled configuration, described above, in which rod member 300 and shank 100 are fixed relative to one another, while head 200 is axially translatable and pivotably movable with respect to shank 100 and rod member 300 so as to permit angulation between the shank and the head.

Referring to FIGS. 5-7, and as mentioned above, head 200 includes a first chamber 230a, having a first diameter, positioned at a proximal, or upper portion of head 200, and a second chamber 230b, having a second diameter, positioned at a distal, or lower portion of head 200. The diameter of first chamber 230a is larger than the diameter of a proximal opening of second chamber 230b such that a shoulder 234 is defined therebetween. As shown, the diameter of the first chamber 230a is substantially uniform between the proximal and distal ends of the first chamber 230a. However, it is contemplated that the proximal opening of first chamber 230a may have a larger diameter than the distal opening of first chamber 230a thus defining a generally conical or tapered configuration while maintaining the diameter of the distal opening greater than the proximal opening of second chamber 230b, thereby defining the shoulder 234. A plurality of longitudinal slots 232 is defined on inner surface 231 of first chamber 230a of head 200, extending from the proximal end 202 of head 200 to shoulder 234. Accordingly, as discussed above, the complementary-shaped proximal portion 330 of rod member 300 (FIG. 4) is able to translate through first chamber 230a of head 200 within slots 232. Proximal portion 330 has a smaller diameter than first chamber 230a but a larger diameter than the proximal opening of second chamber 230b such that proximal portion 330 may translate through first chamber 230a until proximal portion 330 contacts shoulder 234, which inhibits further distal translation. The second chamber 230b has proximal and distal openings. As described hereinabove, the proximal opening of the second chamber 230b has a diameter less than the diameter of the distal opening of the first chamber 230a. Further, the second chamber has a distal opening with a diameter that is greater than the diameter of the proximal opening of the second chamber 230a. As shown, the diameter of the second chamber 230b increases from the proximal end near shoulder 234 towards the distal end and defines a tapered or chamfered opening. Head 200 is preferably constructed of a relatively hard material, such as titanium alloy. More specifically, head 200 may be constructed of Ti-6Al-4V. As best seen in FIG. 6, the width of helical threading 222 on the outer surface of head 200 tapers slightly from a proximal end 202 to a distal end 204 of head 200, such that head portion 220 is wider at the proximal end 202 as compared to the distal end 204.

Figure 8:
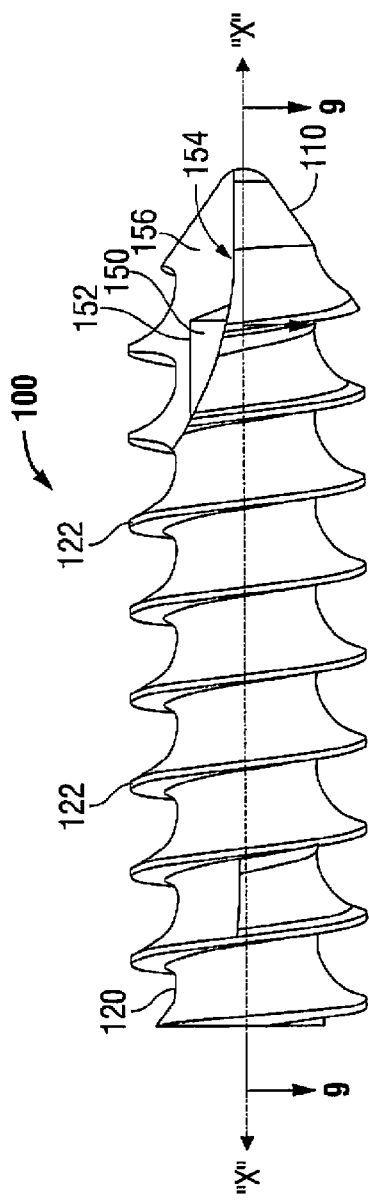
FIG. 8 is a side view of the shank of the bone screw of FIG. 1.
Figure 9:
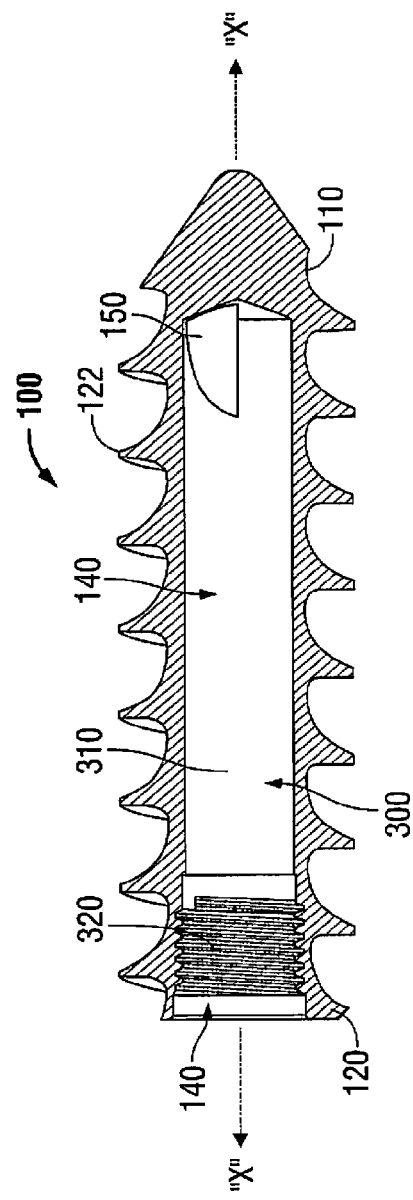
FIG. 9 is a side, cross-sectional view of the bone screw of FIG. 8, taken along section line 9-9 of FIG. 8.

Referring now to FIGS. 8-9, the distal end 110 of shank 100 may be configured such that bone screw 10 is a "self-starting" or "self-drilling" screw 10. Alternatively, distal end 110 may be configured such that bone screw 10 is a "self-tapping" bone screw 10. Further, the bone screw 10 may be configured such that the physician would drill and tap a hole in the selected bone structure prior to inserting the bone screw 10. In any configuration, distal end 110 includes first and second side walls 154 and 156 that define a flute section 150 including flute cut 152 (see FIG. 4). The first and second sidewalls 154, 156 of the flute section 150 extend from the pointed tip portion 110 to a crest of thread 122 near the distal end 110 of shank 100. The first sidewall 154 is planar and is aligned along a central longitudinal axis "X" of the shank 100 such that first sidewall 154 is coplanar with the longitudinal axis "X." The second side wall 156 further includes a planar portion that is parallel to the central longitudinal axis "X" and an arcuate portion that extends proximally from the planar portion. Similarly, third and fourth side walls (not shown) are defined opposite first and second side walls 154, 156 at distal end 110 of shank 100. Although not shown in the drawings, the flute defined by the third and fourth side walls also includes a flute cut that is substantially similar to flute portion 150, and is diametrically opposed to flute portion 150 with respect to longitudinal axis "X." As mentioned above, once rod member 300 is inserted and threadably engaged with shank 100, distal end of rod member 300 is laser welded to shank 100 along flute cuts 152 of both flutes 150. As best shown in FIG. 9, central lumen 140 extends distally from open proximal end 120 of shank 100. Lumen 140 extends only partially through shank 100 and is dimensioned to have a diameter that is slightly larger than a diameter of elongated body portion 310 of rod member 300 such that rod member 300 may be disposed therethrough, as shown in FIG. 3.

Figure 10:
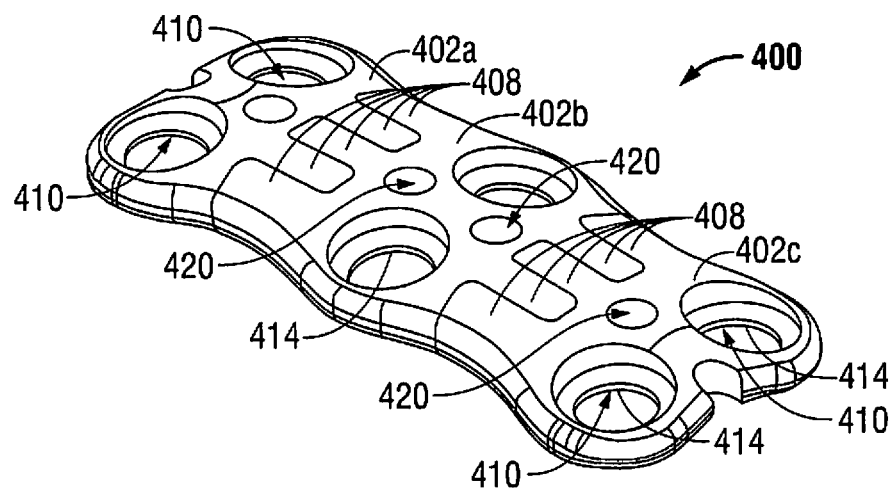
FIG. 10 is a perspective view of a dynamic bone plate in accordance with one embodiment of the present disclosure.

Referring now to FIG. 10, an implant, such as bone plate 400, is shown having a first end section 402a, a middle section 402b, and a second end 402c. Bone plate 400 is shown in a contracted state, wherein sections 402a, 402b and 402c are in close proximity with one another. Bone plate 400 is adjustable to an expanded state wherein sections 402a, 402b and 402c are in a relatively spaced apart position, such that gaps are defined between the adjacent plate sections. Interlocking teeth 408 are separable, to allow for the expansion and retraction of sections 402a, 402b and 402c with respect to one another.

Each of plate sections 402a, 402b, and 402c of the bone plate 400 may be manufactured from commercially pure titanium. In addition, bone plate 400 may be available in different configurations (e.g., size, type of metal used, etc.) and may be anodized into different colors (e.g., green, blue, purple, etc.) to indicate the specific configuration of the plate member to the user. Further, depending on the procedure to be performed, the plate 400 may include more or fewer plate sections 402a, 402b, 402c.

Additionally, each of plate sections 402a, 402b, and 402c has a radius of curvature along its longitudinal axis and a radius of curvature (e.g., 1.5 inches) along its lateral axis such that the bone plate 400 as a whole may conform to adjacent vertebral bodies of a patient's spine. In instances where the implant (e.g. bone plate 400) spans adjacent bone structures (e.g. vertebral bodies), movement of the adjacent bone structures towards or away from each other is accommodated by the pivotable (i.e. angular) movement of shank 100 relative to head 200. In particular, the pivotable movement of shank 100 relative to head 200 allows for normal subsidence in spinal procedures where a bone graft is disposed between adjacent vertebral bodies and the adjacent vertebral bodies move towards each other as the bone graft is assimilated into the adjacent vertebral bodies. Although discussed in terms of a bone plate, the pivotable features of the bone screw 10 are equally applicable with other bone implants such as those where one portion of the implant is fastened or anchored to a fixed location and the bone screw 10 is positioned at another location on the implant.

The bone plate 400 has a top surface and a bottom surface defining the thickness of the bone plate 400. In addition, bone plate 400 includes a plurality of screw openings 410 and one or more guide openings 420, wherein the screw openings 410 and one or more guide openings 420 extend through the thickness of the bone plate 400. The one or more guide openings 420 are positioned along the central longitudinal axis of the bone plate 400. Each of the screw openings 410 includes a lip 414 located on the annular sidewall of the screw opening 410. The lip 414 is configured for engaging the head 200 of screw 10 (FIG. 1) such that threads 222 of head 200 of screw 10 engage the lip 414. Head 200 may be screwed into plate 400 until distal end 202 of head 200 is flush with the top surface of plate 400. It is contemplated that the head 200 may not be flush with the top surface of the plate 400. As can be appreciated, the increased width of head 200 from distal end 202 to proximal end 204 creates a tighter engagement between head 200 and lip 414 as head 200 is threaded, or screwed, into plate 400. Further, since the plate 400 (and lip 414) is made of titanium (e.g. commercially pure titanium), a softer material than titanium alloy (e.g. Ti-6Al-4V), when head 200 is advanced through screw opening 410, threads 222 of head 200 engage the corresponding lip 414 to deform the lip 414 and secure head 200 within the screw opening 410. These above-mentioned features help keep head 200 fixed within screw opening 410 and inhibit the head 200 from backing out of the screw opening 410. This type of screw locking arrangement is disclosed and shown in U.S. Pat. No. 6,322,562 to Wolter, the entire contents of which are hereby incorporated by reference herein.

Figure 11:
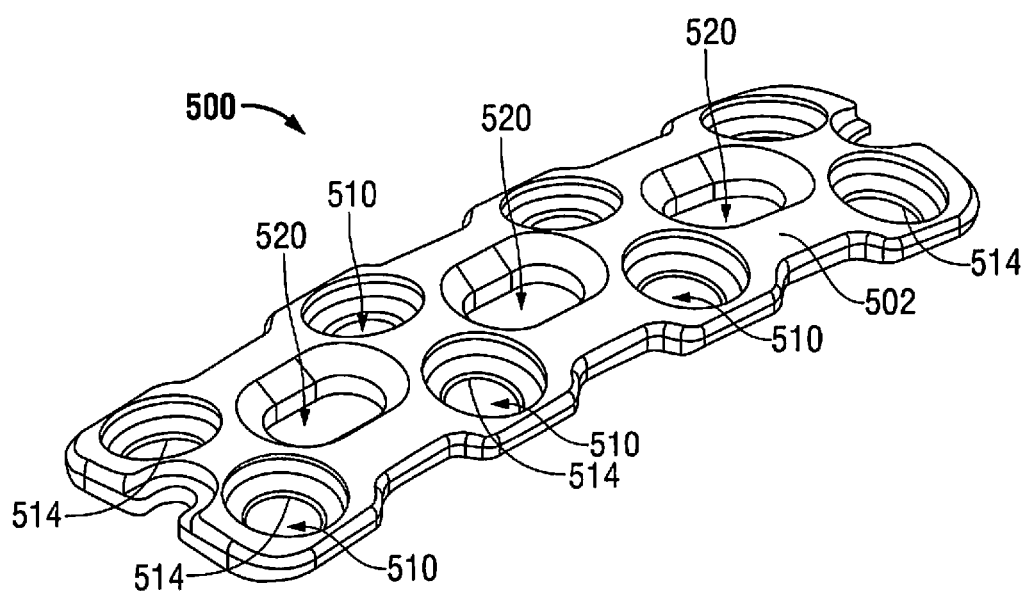
FIG. 11 is a perspective view of a bone plate in accordance with another embodiment of the present disclosure.

An alternate implant, such as bone plate 500, is shown in FIG. 11. Bone plate 500 has the same essential features as bone plate 400, however, bone plate 500 has a uniform, stationary body 502 that is configured in a one-piece configuration. Bone plate 500 is substantially similar to bone plate 400, other than the fact that bone plate 500 is stationary, rather than expandable. Similarly to bone plate 400, bone plate 500 has a top surface and a bottom surface, a plurality of screw openings 510 and one or more guide openings 520. The screw openings 510 and one or more guide openings 520 extend through bone plate 500. The one or more guide openings 520 are positioned along the central longitudinal axis of the bone plate 500. Each of the screw openings 510 has a lip 514 located therein in proximity to the bottom surface of the bone plate 500. Lip 514, as with lip 414 of plate 400, is configured for engaging a head 200 such that rotating the head 200 causes the threads 222 of head 200 to engage and deform the lip 514, fixing head 200 therein. As with bone plate 400, bone plate 500 may be smaller or larger than the bone plate 500 shown in FIG. 14, depending on the procedure to be performed. In order to provide the advantages of locking engagement between the head made of a material having greater hardness than the lip, and yet also provide maximal opportunity for material selection choices between the screw head and plate, it is contemplated that the lip may be provided as part of an insert into the plate hole. In this manner, the entire plate need not be made of a material of lower hardness than the screw head. By way of example, the screw head may be formed of titanium alloy, a plate hole insert containing the lip may be formed of commercially pure titanium, and the plate may be formed of PEEK, titanium alloy, cobalt chrome or any other suitable material irrespective of the relative hardness between the screw head and the lip insert.

The operation of bone screw 10 in conjunction with bone plate 400 will now be described in detail with reference to FIGS. 1-11. Although reference hereinbelow is made to bone plate 400, it is contemplated that the same operation applies to bone screw 10 in conjunction with plate 500 and thus, the description of such will not be repeated. As mentioned above, during assembly of screw 10, rod 300 is inserted through lumen 210 of head 200 and into lumen 140 of shank 100. Rod 300 is then engaged to shank 100 via the engagement of threads 320 with threads 142. In order to fix the screw 10 in this configuration, rod member 300 is laser welded to shank 100 at the flute cuts 152 at distal end 110 of shank 100. Once assembled, screw 10 is ready for use.

Initially, plate 400 is adjusted, e.g., plate portions 402a, 402b, 402c are moved to the expanded position, according to the size required for the specific procedure. Next, plate 400 is positioned on the vertebrae such that bottom side of plate 400 is abutting a surface of bone and such that the screw openings 410 are positioned where the screws 10 are to be driven into bone. Distal end of shank 100 of screw 10 is then inserted from the top side of plate 400 and through a screw opening 410 in plate 400, such that distal tip 110 of shank 100 is adjacent a surface of bone. A screwdriver, or driving tool (not shown) having a complementary shape, e.g. hexagonal configuration, to the shape of lumen 210 of head 200 is then engaged with head 200. The driving tool (not shown) is then rotated, thereby rotating and driving shank 100 into bone due to the pitched threading 122 disposed on shank 100. Rotation of the driving tool (not shown) causes simultaneous rotation of the head portion 200, rod member 300, and shank 100 due to the complementary-shaped engagement of the driving tool (not shown) with inner surface 231 of first chamber 230a of head 200 and due to the complementary-shaped engagement of the inner surface 231 with the proximal portion 330 of rod member 300. In other words, the engagement of the driving tool (not shown) and proximal portion 330 of the rod member 300 allows all the components (shank 100, head 200 and rod member 300) of screw 10 to rotate upon rotation of the driving tool (not shown). Alternatively, the physician may prepare the hole using a drill and a tap the hole prior to inserting the bone screw 10.

As the driving tool (not shown) is further rotated to further drive shank 100 into bone, distal end 202 of head 200 eventually enters screw opening 410 of screw plate 400. At this point, further driving of shank 100 into bone simultaneously causes head 200 to be driven into screw opening 410. As described above, head 200 is screwed into opening 410 via the engagement and deformation of lip 414 with threading 222 on outer surface 220 of head 200. Screw 10 is tightened such that shank 100 is secured within bone and such that head portion 200 is secured within plate 400, as described above. In this position, shank 100 (and thus rod member 300) is fixedly engaged with bone, and head portion 200 is fixedly engaged with plate 400. However, due to the relationship between head 200 and shank 100 and rod member 300, wherein head 200 is axially translatable and pivotally moveable with respect to shank 100 and rod member 300, plate 400 is still moveable with respect to bone. In other words, plate 400 is not rigidly attached to bone, but, rather, some play exists between plate 400 and bone even though screws 10 are sufficiently securing plate 400 to bone.

Insertion of the remaining screws 10 through the respective screw openings 410 of plate 400 can then be performed as described above, until plate 400 is fully secured to bone.

It will be understood that various modifications may be made to the embodiments of the presently disclosed bone screw. The aforementioned principles are applicable to any implant using a bone screw for fastening the implant to bone. In addition, although not preferred, it is contemplated that a thread rather than a lip may be provided in the implant hole (whether formed in the implant or as part of an insert), such that the threads on the screw head threadably engage threads provided in the implant hole. It is further contemplated that other mechanisms could be used in place of the engagement of threads on the screw head with the lip to secure the screw head to the implant. Thus, additional structures such as a cover plate (whether as a separate structure applied to the implant or pre-attached to the implant) to cover the screw head and prevent back-out, a set screw to lock the screw head to the plate and other such structures could be used in place of or in addition to the threaded screw head and lip engagement described herein and preferred. Therefore, the above description should not be construed as limiting, but merely as exemplifications of embodiments. Those skilled in the art will envision other modifications within the scope and spirit of the present disclosure.

What is claimed is:

1. A bone screw assembly comprising:
    a shank defining a lumen extending at least partially therethrough from a proximal end thereof, the shank defining at least one window towards a distal end thereof, the at least one window providing access to the lumen from an exterior of the shank;
    a head defining a lumen therethrough; and
    a rod member configured for insertion through the lumen of the head and into the lumen of the shank, the rod member being laser welded to the shank through the at least one window and moveably coupled to the head such that both the rod member and the shank are moveable with respect to the head.

2. The bone screw assembly according to claim 1, wherein a helical thread is formed on an outer surface of the shank to facilitate insertion into bone.

3. The bone screw assembly according to claim 1, wherein the rod member includes a neck portion at a proximal end of the rod member, the neck portion being threadably engageable with an inner surface of the shank.

4. The bone screw assembly according to claim 3, wherein the rod member includes an outwardly protruding annular flange disposed at a distal end of the neck portion, the annular flange being complementary in shape to an inner surface of the head and configured to sit on a shoulder positioned on the inner surface of the head.

5. The bone screw assembly according to claim 4, wherein the annular flange includes a plurality of protrusions extending therefrom, each protrusion configured to engage a slot defined within the inner surface of the head.

6. The bone screw assembly according to claim 1, wherein the shank is pivotable with respect to the head.

7. The bone screw assembly according to claim 6, wherein the head includes a helical thread formed on an outer surface thereof for engaging a lip provided in an opening in an implant.

8. The bone screw assembly according to claim 7, wherein the head is constructed of a material which is harder than a material of the lip of the opening in the implant, such that the lip is deformed upon coupling the head to the implant.

9. The bone screw assembly according to claim 8, wherein the head is formed of a titanium alloy.

10. The bone screw assembly according to claim 1, wherein shank includes at least one flute defined therein at a distal end thereof, the flute including the at least one window extending therethrough.

11. The bone screw assembly of claim 6, wherein rotation of the shank in a first direction causes rotation of the head in the first direction.

12. An implant assembly comprising:
    an implant including at least one opening defined therein, the at least one opening configured for insertion of a bone screw therethrough;
    at least one bone screw, each bone screw including:
        a shank having an open proximal end and defining a lumen partially therethrough, the shank including a continuous helical thread disposed on an outer surface of the shank, the shank defining at least one window towards a distal end thereof that provides access to the lumen from an exterior of the shank;
        a head having a lumen defined therethrough, an inner surface of the head having a plurality of slots defined therein, the head being securable within one of the openings in the implant;
        a rod member, the rod member including a shaft and a flange portion, the flange portion including a plurality of outwardly extending protrusions shaped complementarily to the plurality of slots; and
    wherein, the shaft of the rod member is insertable through the lumen of the head and into the lumen of the shank, the shaft of the rod member being laser welded to the shank through the at least one window, the plurality of protrusions being configured to sit within the plurality of complementary-shaped slots such that the rod member and the shank are moveable with respect to the head.

13. The implant assembly according to claim 12, wherein the implant includes a bone plate having a plurality of openings, each opening configured for receiving a bone screw therethrough.

14. The implant assembly according to claim 13, wherein the bone plate includes a plurality of sections that are moveable with respect one another such that the bone plate is moveable between an expanded and a contracted position.

15. The implant assembly according to claim 13, wherein the head includes a helical thread formed on an outer surface thereof for coupling with one of the openings in the bone plate.

16. The implant assembly according to claim 13, wherein the head is constructed of a material which is harder than a material of a lip of the opening in the bone plate such that the lip is at least partially deformed upon coupling of the head therein.

17. The implant assembly according to claim 13, wherein the rod member and the shank are pivotable relative to the head.

18. A bone screw assembly comprising:
    a shank defining a lumen extending at least partially therethrough from a proximal end thereof, the shank defining at least one window towards a distal end thereof, the at least one window providing access to the lumen from an exterior of the shank;
    a head; and a rod member configured for insertion through the lumen of the head and into the lumen of the shank, the rod member being laser welded to the shank through the at least one window and being couplable to the head.

19. The bone screw assembly according to claim 18, wherein the rod member is moveably couplable to the head such that both the rod member and the shank are moveable with respect to the head.

\* \* \* \* \*